United States Patent [19]

Durrani

[11] Patent Number: 6,159,491
[45] Date of Patent: Dec. 12, 2000

[54] PROLONGED RELEASE BIOADHESIVE VAGINAL GEL DOSAGE FORM

[75] Inventor: Manzer J. Durrani, Waltham, Mass.

[73] Assignee: Biovector Technologies, Inc., New York, N.Y.

[21] Appl. No.: 09/250,123

[22] Filed: Feb. 12, 1999

[51] Int. Cl.[7] .................... A61F 6/06; A61F 13/02
[52] U.S. Cl. ............................ 424/430; 424/434
[58] Field of Search .................... 424/430, 434

[56] References Cited

U.S. PATENT DOCUMENTS

| | | | |
|---|---|---|---|
| 3,865,108 | 2/1975 | Hartop | 128/260 |
| 4,226,848 | 10/1980 | Nagai et al. | 424/19 |
| 4,250,163 | 2/1981 | Nagai et al. | 424/14 |
| 4,615,697 | 10/1986 | Robinson | 604/890 |
| 4,707,362 | 11/1987 | Nuwayser | 424/433 |
| 4,708,834 | 11/1987 | Cohen et al. | 264/4.3 |
| 4,755,378 | 7/1988 | Buxton et al. | 424/80 |
| 4,795,436 | 1/1989 | Robinson | 424/422 |
| 4,983,392 | 1/1991 | Robinson | 424/427 |
| 4,983,393 | 1/1991 | Cohen et al. | 424/430 |
| 5,008,117 | 4/1991 | Calanchi et al. | 424/494 |
| 5,069,906 | 12/1991 | Cohen et al. | 424/430 |
| 5,225,196 | 7/1993 | Robinson | 424/427 |
| 5,330,761 | 7/1994 | Baichwal | 424/469 |
| 5,455,046 | 10/1995 | Baichwal | 424/457 |
| 5,472,704 | 12/1995 | Santus et al. | 424/435 |
| 5,474,768 | 12/1995 | Robinson | 424/78.31 |
| 5,478,574 | 12/1995 | Baichwal et al. | 424/485 |
| 5,587,175 | 12/1996 | Viegas et al. | 424/427 |
| 5,624,675 | 4/1997 | Kelly | 424/405 |
| 5,650,192 | 7/1997 | Britton et al. | 427/2.19 |
| 5,667,492 | 9/1997 | Bologna et al. | 604/57 |
| 5,672,356 | 9/1997 | Rault et al. | 424/468 |
| 5,700,486 | 12/1997 | Canal et al. | 424/501 |
| 5,714,159 | 2/1998 | Shalaby | 424/426 |
| 5,759,520 | 6/1998 | Sachetto | 424/45 |
| 5,783,212 | 7/1998 | Fassihi et al. | 424/472 |
| 5,817,343 | 10/1998 | Burke | 424/489 |
| 5,824,343 | 10/1998 | Ng et al. | 424/486 |

*Primary Examiner*—Carlos A. Azpuru
*Attorney, Agent, or Firm*—Pennie & Edmonds LLP

[57] ABSTRACT

The present invention relates to a bioadhesive, prolonged release vaginal gel dosage form comprising a synergistic formulation of carrageenan, acrylic acid containing polymers, agarose and an effective amount of a therapeutic agent, whereby the therapeutic agent is released from this composition initially at a first relatively high rate, to provide a loading dose of the therapeutic agent, followed by a second, lower rate of release that provides a constant, maintenance dose of the therapeutic agent for up to 24 hours. More specifically, the present invention includes compositions within which the agarose is ultra low gelling temperature agarose and the acrylic acid containing polymer may be carbophil, a copolymer of acrylic acid and divinyl alcohol, a copolymer of acrylic acid and $C_{10}$ to $C_{30}$ alkyl acrylic acid or a polyacrylic acid homopolymer.

27 Claims, No Drawings

PROLONGED RELEASE BIOADHESIVE VAGINAL GEL DOSAGE FORM

FIELD OF THE INVENTION

The present invention relates to bioadhesive compositions for the controlled release of therapeutic agents. This invention also relates to a process for making the bioadhesive compositions and a method of treatment, comprising intravaginal administration of the bioadhesive composition comprising the therapeutic agent. The present invention is further directed toward a bioadhesive composition providing both an initial loading dose of the therapeutic agent through an initially higher rate of release as well as providing a second, sustained dose, by means of an additional, lower rate of release of the therapeutic agent.

BACKGROUND OF THE INVENTION

Prolonged release formulations of therapeutic agents provide patients with more uniform levels of the active agent over extended periods of time. Consequently sustained release formulations allow the therapeutic agent to be administered less frequently providing improved convenience to the patient as well as enhanced compliance over alternative, more cumbersome dosage regimens. Sustained release of a therapeutic agent is particularly important in order to avoid substantially fluctuating concentration of the drug in the patient, particularly for active agents having relatively short half-lives.

Uniform dispersion of an active agent within an erodible matrix has been employed as one approach to the formulation of sustained release materials. U.S. Pat. No. 5,817,343 discloses a method for forming micro particles containing therapeutic agents. The process comprises dissolving a polymer in an organic solvent along with a co-dissolved or suspended drug. The solvent is removed, leaving a solid drug-polymer matrix that is cooled to a temperature below the glass transition temperature for the matrix and then fragmented to provide asymmetric micro particles. Suitable polymers for use in this method include poly(lactic acid) and poly(lactic acid-co-glycolic acid). Sustained release of the active agent results from the hydrolysis of these polymers in vivo, which gradually erodes the matrix, thereby allowing the therapeutic compound or compounds to diffuse into the body.

A further example of a biocompatible, erodible polymer useful in the formation of prolonged-release matrices comprising therapeutic agents is provided by U.S. Pat. No. 5,834,343. This patent discloses the formation of polymeric ortho ester matrix component materials by reacting monomeric ortho esters with suitable triols in an appropriate solvent. Polymers formed by this method are dissolved in an organic solvent providing a viscous solution into which a therapeutic agent may be mixed. Removal of the solvent yielded a matrix comprising the active agent in a form that can be shaped into a bioerodible implant. Sustained release of the drug is afforded by the acid lability of the ortho ester linkage of the polymer comprising the matrix. The rate of hydrolysis of these linkages can be manipulated by the inclusion of acidic or basic excipients in formulations comprising the ortho ester polymers, thereby varying the rate of release of the active agent from the matrix.

More complex and sophisticated compositions and systems for the controlled, sustained release of therapeutic agents within the body have been developed and formulated as pills, capsules and microcapsules. U. S. Pat. No. 5,783,212 discloses a controlled release pharmaceutical tablet fabricated with at least three layers, each of which comprises swellable, erodible biocompatible polymers. Controlled release is obtained by formulating exterior barrier layers that erode more rapidly than the internal, drug-containing layer, permitting the active agent to diffuse into the local environment as the barrier layers degrade. As the barrier layers erode, water diffuses to the drug-containing layer allowing the active agent to diffuse through the swollen barrier layer. Appropriate formulation of the barrier layers, both with respect to their composition and relative thickness as compared with the drug-containing layer, provides a tablet yielding a constant rate of release of the drug within the body. The tablets disclosed, therefore, display "zero-order" release of the therapeutic agent, that is, the amount of drug released remains constant with respect to time. Representative swellable polymers used in the formulation of the individual layers of the tablet disclosed in this patent include polyethylene oxide, hydroxypropylmethylcellulose and carboxymethylcellulose.

An alternative mechanism of controlled drug release within the body is disclosed in U.S. Pat. No. 5,069,906 and U.S. Pat. No. 4,983,393. These patents disclose an intravaginal device constructed as a semisolid gel composition, comprising a therapeutic agent, capable of dissolution or disintegration in the presence of vaginal fluids. The solid gel matrix including the biologically active material consists of an aqueous solution containing a gelling agent dispersed or dissolved therein. Suitable gelling agents include agarose or agar, glycosaminonglycans, collagen, carageen or carrageenan, locust bean gum, fibrin and glycerine. Erosion of the matrix, facilitating the diffusion of the therapeutic agent, is effected in part by the inclusion within the formulation of degradative enzymes selected from the group consisting of protease, agarase, collagenase and saccharidase that hydrolyze the constituent polymers, thereby leading to controlled disintegration and dissolution of the intrauterine device.

Improved drug delivery systems have been provided by the development and application of biocompatible bioadhesive materials, which, in combination with prolonged release formulations, provide sustained release of therapeutic agents within particular regions of the body over extended periods of time.

U.S. Pat. No. 4,226,848 discloses a treatment method comprising administration of a therapeutic composition capable of adhering to the oral or nasal mucosa. The composition comprises a water-swellable and mucosa-adhesive polymeric matrix made up of a cellulose ether and an acrylic acid polymer, in combination with a therapeutic agent dispersed within the matrix. The medicament is released at a controlled rate and is absorbed through the mucosa of the oral or nasal cavity. This patent teaches that the individual components are, preferably, mixed as very fine powders that may be formed into an appropriate shape.

U. S. Pat. No. 5,714,159 and U. S. Pat. No. 5,700,486 disclose bioadhesive sustained release, biodegradable matrices comprising therapeutic agents, formed from compositions made up of three components. The first component comprises synthetic, block copolymeric chains with self-solvating elements to allow its existence as a viscous material at room temperature. The second component is an absorbable, microporous low molecular weight polyester which is highly crystalline and practically insoluble in the first component. The third component, designated a plasticizer, is generally a low molecular weight compound selected, for example, to aid the dispersion of the second component in the first component, to reduce the overall viscosity of the mixture of the first and the second components or to increase the rate of hydration of the mixture. The active agent may be adsorbed carrier materials or mixed with the three components forming the matrix. The materials of this invention provide hydrogel-forming, self-solvating, absorbable polyester copolymers capable of selective, segmental association into compliant hydrogels upon contacting an aqueous environment, allowing the controlled release of entrained biologically active agents.

U.S. Pat. Nos. 4,615,697; 4,795,436; 4,983,392; 5,225, 196 and 5,474,768 issued to Robinson, disclose a bioadhesive polymer for use in controlled release formulations comprising treating agents. The bioadhesive is a water-swellable, but water insoluble, fibrous cross-linked carboxy-functional polymer in which at least 80% of the monomeric units contain at least one carboxyl functionality. These patents define bioadhesives as materials which adhere to biological surfaces such as mucus membranes or skin tissue. These references quantitate bioadhesion as the force required to separate two layers of stomach tissue that are adhered together by an adhesive. The active agent may be combined with the controlled release, bioadhesive, formulation either by mixing the corresponding dry solids or by swelling the bioadhesive in an aqueous medium containing the treating agent, whereby the treating agent is sorbed onto or into the swollen particles of bioadhesive material. Although the bioadhesive materials may serve as the dose rate-controlling medium in these compositions, the rate of controlled release is generally provided by a medicinally inert matrix. Examples of materials used to form this inert matrix include cross-linked human or bovine serum albumin, cross-linked gelatin, poly(2-hydroxyethyl methacrylate), alkyl cellulose ethers, ethylene vinyl acetate copolymers and ethylene propylenediene copolymers. These materials provide controlled release by gradual dissolution or erosion of the matrix through a dispersion mechanism, thereby providing a fresh supply of the treating agent from the matrix in the presence of, for example, gastric or vaginal secretions.

U.S. Pat. No. 5,667,529 discloses a composition comprising the cross-linked polycarboxylic acid polymer of Robinson formulated with nonoxynol-9, a contraceptive with demonstrated activity against human immunodeficiency virus and other biological agents responsible for the spread of sexually transmitted diseases. Preparation of the compositions disclosed includes separate hydration of the polymers, mixing of the water-soluble components and formulation of the oil soluble ingredients. Once the polymers have been hydrated, the active agent, nonoxynol-9 is added and mixed until a uniform preparation is obtained in which the nonoxynol-9 is reversibly associated with the polymer. The oil soluble fraction is then added and the two phases are mixed thoroughly until a uniform composition is obtained. Finally, the pH of the mixture is adjusted to ~pH 4 with sodium hydroxide.

U.S. Pat. No. 5,672,356 discloses bioadhesive pharmaceutical compositions for the controlled release of biologically active materials both locally across the buccal cavity as well as systemically across a mucus membrane. The compositions described comprise an active agent combined with two other compounds. The latter materials are selected from two separate groups, the first comprising one or more copolymers of methyl vinyl ether and maleic anhydride, while the second group includes one or more compounds exemplified by polyvinlypyrrolidone, polyvinyl alcohol, polyethylene glycol, alginic acid and its derivatives, cellulose and derivatives thereof, starches, gums, carraghenates, proteins and cyclodextrins. Bioadhesion is established through the binding of one or more of the compounds of the pharmaceutical dosage form to functional chemical groups at the surface of the biological tissue. The nature of the interactions involved may be described as physical, mechanical or chemical.

U.S. Pat. No. 5,472,704 also discloses a bioadhesive pharmaceutical composition for the controlled release of medicinal drugs. The characteristic feature of the composition is the formation of a plurality of small-size units capable of ensuring a gradual release of the active ingredient contained within each unit coupled with a separate bioadhesive polymer layer coating the individual units. Therefore, the microunits comprise a core containing the active agent and a polymer film coating determining the controlled release of the active ingredient and a separate, bioadhesive polymeric coating that completely envelops the core. Examples of bioadhesive polymers useful for this coating include polyacrylic polymers, cellulose derivatives, natural polymers and mixtures thereof.

The controlled release microunits include reservoir, matrix, osmotic and biodegradable microunits. Reservoir units comprise an inert permeable membrane, having specific diffusion characteristics, that encases a solution of the active material. If the solution of the active material is saturated, a zero-order drug release profile is obtained; that is, there is a constant rate of release of the active agent. If the solution is not saturated, then a first-order release profile is obtained; that is, there is a decreasing rate of release of the active agent with time. Matrix units comprise active agents dispersed or dissolved uniformly within a rate-controlling polymer. These have a "complex" release profile which depends upon the amount of the active material embedded, the solubility of the active agent in the environment in which it is placed, the nature of the matrix material and the geometry of the device. Osmotic units generally involve tablets containing the active agent coated with a membrane semipermeable to the active agent. Provided that the solution of the active agent within the osmotic unit is saturated, the release profile will, essentially, be at a constant rate until the solution is no longer saturated, after which a first-order profile with a decreasing rate of release of the active agent would be expected. Biodegradable matrix units comprise an active agent dispersed within a polymer matrix, wherein the active agent is gradually released as the polymer erodes through hydrolytic degradation.

U.S. Pat. No. 5,700,586 discloses biocompatible, controlled release pharmaceutical compositions in the form of particles comprising a biodegradable polymer, a polysaccharide jellifying and bioadhesive polymer, an amphiphilic polymer, an agent modifying the interface properties of the particles and a pharmacologically active substance. In one application of the process of this disclosure, a biodegradable polymer, a polysaccharide, and an agent modifying the interfacial interactions are solubilized, with or without a solvent depending on the materials used, in an amphiphilic polymer. The pharmacologically active agent is then dissolved or dispersed within the polymer mixture. The solvent, if used, is removed by evaporation and the particle suspension is centrifuged or filtered, and the collected particles are washed. The residue collected is dried to yield the biocompatible, controlled release particles of this invention. Biodegradable polymers contemplated by this disclosure include polylactic acid, polyglycolic acid, polyhydroxybutyric acid, polycaprolacton, polyorthoesters, polyanhydrides, chitins, chitosan, hyaluronic acid, and collagen. Suitable amphiphilic polymers include polyethyleneglycols, polyvinylpyrrolidone and polyvinylalcohols. Suitable jellifying and/or adhesive polysaccharide polymers include sclerogulucan, xanthan, chitins, and chitosans, cellulose and derivatives, alginates and hyaluronic acid. Agents able to modify the interface properties of the particles comprise surface-active agents including sorbitan esters, polysorbates, lecithins and other phospholipids, stearic acid, stearates and derivatives thereof.

The above-cited references disclose the incremental development of controlled release formulations for therapeutic agents. Initial embodiments comprised active agents that were dispersed throughout polymeric matrices that gradually eroded releasing the therapeutic compounds. This degradation of the matrix could be manipulated, for example, by the incorporation of acid labile linkages into constituent polymers or inclusion of specific hydrolytic enzymes that would degrade the device or structure containing a therapeutic agent. The rate of release of the active agent from these compositions would be expected to depend primarily on the surface area exposed to the biological system being treated. Therefore, first order kinetics would be predicted in which the rate of release of the active agent would decrease with time.

In order to provide a constant rate of release of the therapeutic agent, compositions were developed as tablets, for example, formulated with outer barrier layers that eroded more rapidly than the inner, drug-containing layer. Erosion of the outer layers allowed more an increasingly more rapid diffusion of the drug from the inner layer. Tablets were formulated, based upon these principles and materials, that provided a compensating balance between the decreasing surface area of the tablet and the increasing rate of diffusion, thereby effecting a constant rate of release of the active agent.

In parallel, bioadhesive materials were developed and applied to controlled release formulations. Cross-linked polycarboxylic acid polymers have been used to form matrices within which therapeutic agents have been dispersed, providing controlled release formulations which adhere to the biological surface to which they had been applied. These compositions, therefore, provide prolonged release of the active material at the site of application affording treatment benefits over similar compositions lacking the bioadhesive components disclosed.

One application for bioadhesive materials is their formulation as a separate component used to coat core particles which consist of the active agent dispersed within a controlled release, non-bioadhesive polymer. In this embodiment, the bioadhesive and controlled release components are physically separated in the formulation of "microunits" providing extended administration of pharmacologically active compounds. In an alternative application, a biodegradable polymer is combined with a polysaccharide displaying jellifying and/or bioadhesive properties, an amphiphilic polymer and a surface active agent to facilitate the emulsification of the particles formed by this process. The suspended particles were then separated, washed and dried to provide an alternative controlled released formulation with bioadhesive properties.

In summary, considerable progress has been achieved in the development of controlled-release formulations for therapeutic agents that have been combined with bioadhesive materials allowing localized, sustained release of active agents. However, the compositions disclosed above provide either a constant (zero order kinetics) or a decreasing rate (first order kinetics) of release of the therapeutic agent dispersed or dissolved within the controlled release formulation. Therefore, there remains a need for compositions that exhibit both an initial, faster rate of release of the active agent thereby providing a loading dose for the therapeutic agent, that is followed by a second, slower rate of release providing a constant, sustained rate of release of the pharmacologically active agent.

SUMMARY OF THE INVENTION

The present invention relates to a bioadhesive, prolonged release drug composition comprising a synergistic formulation of carrageenan, acrylic acid containing polymers, agarose and an effective amount of a therapeutic agent. The therapeutic agent is released initially at a first relatively high rate, to provide a loading dose of the therapeutic agent, followed by a second, lower rate of release that provides a constant, maintenance dose of the therapeutic agent for up to 24 hours.

In one embodiment of the present invention, the agarose is ultra low gelling temperature agarose (Fisher Scientific, Pittsburgh, PA.). In another embodiment of this invention, the acrylic acid containing polymer may be polycarbophil, a homopolymer of acrylic acid and divinyl glycol, a copolymer of acrylic acid and $C_{10}$ to $C_{30}$ alkyl acrylate copolymer Pemulen™ TR1, TR2, Carbopol® 1342 or 1382 resin.

In another embodiment, one or more of the therapeutic agents dispersed or dissolved within the bioadhesive, prolonged release drug composition of the present invention, are selected from the group consisting of a spermicide, antiviral, antibacterial, antifungal, antimycotic, antipruritic, emollient, humectant, anti-inflammatory, immunomodulator, hormonal, antineoplastic or an analgesic agent.

A further embodiment of this invention is directed toward a method of administering a therapeutic agent comprising providing a bioadhesive, prolonged release drug composition comprising carrageenan, an acrylic acid containing polymer, agarose and an effective amount of a therapeutic agent and applying this composition to the vaginal mucosa of the patient. This embodiment further contemplates that the therapeutic agent is, or the therapeutic agents are, released initially at a first relatively high rate, to provide a loading dose of the therapeutic agent, followed by a second, lower rate of release that provides a constant, maintenance dose of the therapeutic agent for up to 24 hours.

A still further embodiment of this invention is directed to a method for making a bioadhesive, prolonged release drug composition. This embodiment contemplates first dissolving soluble components, including, but not limited to sodium chloride, methylparaben, acetate buffer, and, optionally, a therapeutic agent in a suitable amount of purified water. The therapeutic agent is added either in the first step or the last step of this process depending upon whether or not heating would be required for dissolution of this material or upon the thermal stability of the specific therapeutic agent employed. The gelling agents, low melting temperature agarose and carrageenan, are gradually added, with stirring, to this first solution until a uniform dispersion is obtained. The acrylic acid containing polymer, selected from the group consisting of polycarbophil, a homopolymer of acrylic acid crosslinked with divinyl glycol, polyacrylic acid homopolymers (Carbopol 974P-NF and Carbopol 971P-NF and other carbomers), and other copolymers of acrylic acid, ETD (easy-to-disperse) resins and copolymers of acrylic acid and $C_{10}$ to $C_{30}$ alkyl acrylic acid, is added slowly, with stirring until dispersed. This mixture, while being stirred, is heated to 90° C. for a short period of time and then cooled to 70° C. for a second short period of time. The mixture is cooled until it reaches room temperature where stirring is continued until the mixture is uniform. If heating is not required for dissolution of the therapeutic agent, or if it is heat labile, it may be stirred into this mixture at room temperature.

In another embodiment of this process for making the bioadhesive, prolonged release drug composition of the present invention, the therapeutic agent is selected from the group consisting of a spermicide, antiviral, antibacterial, antifungal, antimycotic, antipruritic, emollient, humectant, anti-inflammatory, immunomodulator, hormonal, antineoplastic or an analgesic agent.

DETAILED DESCRIPTION OF THE INVENTION

The present invention comprises a bioadhesive, prolonged release vaginal gel dosage form designed to incorporate a therapeutic agent for local or systemic action when administered intravaginally. It is intended for vaginal administration and designed to release initially at a more rapid rate to provide a "loading" dose of the therapeutic agent and then to provide for a prolonged release of the incorporated therapeutic agent for up to 24 hours, depending upon the exact formulation. The gel comprises two natural gelling agents (carrageenan and an agarose derivative) and a third agent (carbophil or copolymers of polyacrylic acid containing $C_{10}$–$C_{30}$ alkyl acrylate groups) that has been incorporated into this formulation in order to minimize syneresis, or a "squeezing out" of the dispersion medium in the gel matrix. Various concentrations of the product can be prepared. This bioadhesive, prolonged release vaginal gel dosage form is designed to be packaged in disposable tubes or vaginal syringes for single-use purposes.

The bioadhesive, controlled release drug delivery system of this invention is based upon the synergistic action of carrageenan, polycarbophil/polyacrylic polymer and agarose polymers, which generates a complex network structure that not only promotes bioadhesion but also forms a diffusional barrier to drug migration, thereby increasing the duration of drug action.

The formulated prolonged-release bioadhesive vaginal gel dosage form disclosed herein provides administration of therapeutic agents over a period of time of up to 24 hours. Although alternative methods of vaginal drug administration are currently available there is still a need for a drug delivery system that can be easily administered, that provides a prolonged administration of the active agent, and provides an administered dosage form that adheres to the vaginal wall and does not fall out, leak out or cause irritation. Examples of therapeutic agents that can be formulated within the prolonged-release bioadhesive vaginal gel dosage form disclosed herein, include, but are not limited to, spermicides for contraception, antibiotics for vaginitis, antipruritics for vaginal itching, humectants and emollients for vaginal dryness, corticosteroids for inflammations, antifungals for fungal infections and antimycotics for mold and yeast infections, anti-cancer agents, antiviral agents and hormones for pre-menstrual syndrome (PMS) and hormone replacement therapy (HRT).

The prolonged-release bioadhesive vaginal gel dosage form disclosed herein is particularly effective for the delivery of therapeutic levels of spermicides. Although there are a number of contraception methods available including oral contraceptives, barriers (condoms, diaphragm), intrauterine devices, spermicides and others, they possess certain disadvantages and/or side effects. They are inconvenient, contain irritating agents, or are expensive. A need exists for an easy-to-administer, safe, nonirritating, rapidly effective prolonged release gel containing a spermicidal agent. The preparation described here consists of naturally derived gelling agents (Carrageenan, ULGT agarose) formulated to provide a prolonged release of an incorporated spermicidal agent (nonoxynol-9) and an agent to prevent syneresis (polycarbophil).

The gel dosage form disclosed herein may readily be formulated to contain between 2 pph (parts per hundred) and 10 pph of nonoxynol-9 in a total volume of approximately 3 mL of the matrix, providing a dosage range of about 60 mg. to about 300 mg. of nonoxynol-9 that falls within the range utilized by the commercial products described below. In vitro studies have shown that about 25% of the nonoxynol-9 is released from the gel matrix in the first 1–2 hours, another 25% is released after 6 hours and the remainder is released continuously for up to 24 hours after administration. Therefore, the formulation disclosed provides for a more rapid initial release of the therapeutic agent followed by a slower, linear rate of release for the remainder of the 24 hour period, yielding a biphasic zero order release profile.

Antibiotic agents incorporated into the gel formulations disclosed herein would allow convenient once-daily administration of these compounds. If the formulation were to be administered in the evening, for example, the prolonged release of the drug throughout the night and into the following day would provide a consistently higher drug concentration in the vagina as compared to other modes of drug administration including conventional vaginal inserts, tablets, suppositories or douches. Antibiotics that could be formulated into the gel dosage form disclosed herein would include, but not be limited to, bacitracin, clindamycin, colistimethate, colistin, lincomycin, metronidazole, novobiocin, polymyxin B, spectinomycin, vancomycin, amikacin, gentamicin, kanamycin, neomycin, netilmicin, streptomycin and tobramycin. Similarly, antifungal agents that could be formulated into the gel dosage form disclosed herein include, but are also not limited to, amphotericin B, fluconazole, flucytosine, griseofulvin, itraconazole, ketoconazole, nystatin and terbinafine. Examples of anti-neoplastic agents that could be formulated into the gel dosage form disclosed herein include, without limitation, 5-fluorouracil, cisplatin and paclitaxel. Anti-viral agents that could be formulated into the gel dosage form disclosed herein include, without limitation, anti-HIV and anti-Herpes agents.

The prolonged release bioadhesive vaginal dosage form of the present invention provides a gel that consists of carrageenan, ultra low gelling temperature agarose, carbophil or polyacrylic acid polymers, sodium chloride, methylparaben, sodium acetate, acetic acid in purified water, and an active drug agent. The polycarbophil can be replaced by copolymers of polyacrylic acid containing $C_{10}$–$C_{30}$ alkyl acrylate groups. The gel is soft, clear to translucent and easily manipulated. Accordingly, this vaginal gel formulation can be administered, conveniently and easily by means of either a vaginal syringe or a suitable applicator. A more detailed description of the individual components of the compositions of the present invention is presented below.

Carrageenan (CAS 9000-07-1; Chondrus, Carrageen, Irish moss, G-379) is a sulfated polysaccharide. It is a hydrocolloid obtained from various members of the Gigartinaceae or Solieriaceae families of the red seaweed, Rhodophyceae. It consists of the sulfate esters of galactose and 3,6-anhydrogalactose copolymers. It is a yellow to white powder that is odorless and tasteless. It is soluble in hot water and in hot concentrated sodium chloride solutions. It is insoluble in oils and in organic solvents. It is used as an emulsifier, binder, extender, stabilizer, thickener, gelling agent, suspending agent, bulk laxative and is used in oral and topical products; it is soothing to the skin. It is commonly used in 1 to 5% concentrations. It is manufactured and distributed in both pharmaceutical and food products. Example trade names include Aquagel SP 399; Cl-10, CM-80, Cracked Bleached Irish Moss, Genu Carrageenan, Genugel Series, Genuvisco, Soageena, Soageena LX7, Soageena LX26, Soageena WX87, Stamere CK0S, Stamere-325, Stamere-350, Stamere-350S, Stamere NI. Carrageenan is soluble in 30 parts of water at 80° C. forming a viscous clear or slightly opalescent solution. Dispersion is more readily achieved when an initial mixture is prepared using ethanol, glycerol, or syrup. The maximum stability of carrageenan is obtained at pH values between 4 and 10.

Ultra low gelling temperature agarose is a neutral, gelling fraction of agar usually provided as a white to slightly off-white dry powder that is nonhygroscopic, and easily cast into gels. It forms a macroporous matrix which allows rapid diffusion of high molecular weight macromolecules without significant restriction by the gel. These gels have a high gel strength, are nontoxic and, unlike polyacrylamide, contains no potentially damaging polymerization by-products. There is no free-radical polymerization involved in agarose gelation. Agarose gels are thermoreversible and can be air dried to transparent films. Agarose is a specialty "soft agarose" product with ultralow gelling and melting temperature properties. It produces a clear gel that may be stored, when sterile, almost indefinitely. The gels may be melted at 40–50° C. and can be stored at room temperature. The approximate molecular range is from 50,000 to 600,000 daltons. The powder has less than 10% moisture, less than 0.10% sulfate, and a gel strength of about 75 g/cm$^2$ (2% gel). ULGT Ultra low gelling temperature agarose is prepared by the controlled introduction of hydroxyethyl groups to the agarose molecule. Chemical modification in the form of alkylation with hydroxyethyl residues allows for the ultra low gelling temperature (around 40° C.). The addition of chaotropic or other agents which modify the surface tension of water (e.g., nonoxynol-9) further changes (lowers) the gelling and melting temperature of the polysaccharide. The combination of nonoxynol-9, for example, and agarose melts slowly within the range of 37° C. and 40° C. The reduction in gelling temperature from the natural agarose value of about 36° C. is a function of the degree of hydroxyethylation. Two consequences of the hydroxyethylation of agarose are a reduction in gel strength and an increase of gel clarity. The gelling temperature, melting temperature and gel strength vary dependent upon the concentration of the agarose in the gel.

Polycarbophil (Noveon AA-1, acrylic acid crosslinked with divinyl alcohol) homopolymer occurs as a white to creamy white granular material, having a slight, characteristic, ester-like odor and contains a maximum of 1.5% water. It will swell upon contact with water but is insoluble in water and is insoluble in most organic solvents. It is a pharmacologically inert substance that has the capacity to bind free water, hence its used in diarrheal disorders to decrease the fluidity or looseness of stools. It is a component of the commercial products "Replens" (Columbia) for treating vaginal dryness, and "Fiberall" (Ciba Consumer) for treating constipation.

Polyacrylic acid polymers (Pemulen TR1, TR2; B.F. Goodrich, Brecksville, Ohio) and others, have excellent stability, high efficiency, low irritancy at low usage levels. They are compatible with a broad range of nonionic or slightly ionic water soluble materials. They are normally mildly acidic polymers and hydrogen bond in solution, resulting in increased viscosity of the system.

Sodium chloride is available as a white crystalline powder or as colorless crystals. It has a saline taste and is used in a variety of parenteral and nonparenteral pharmaceutical formulations. In parenteral, ophthalmic and nasal preparations, it is used to prepare isotonic solutions. It is also used as a capsule diluent, lubricant, to control drug release from some microcapsules, to control micelle size and to adjust the viscosity of some polymer dispersions by altering the ionic character of the formulation. The pH of a saturated solution is in the range of 6.7 to 7.3 and it is soluble in water (1 g in 2.8 mL), glycerin (1 g in 10 mL) and 95% ethanol (1 g in 250 mL). An 0.9% w/v aqueous solution is iso-osmotic with serum and its solutions are stable. It can also decrease the solubility of methylparaben in aqueous solution. The 0.9% Sodium chloride solution contains not less than 95.0% and not more than 105.0% of the labeled amount of sodium chloride in water for injection. As an isotonic solution, it contains 0.9 gram of sodium chloride per 100 mL of solution. It has a pH between 4.5 and 7.0 and contains no added antimicrobial agents. Sodium chloride solutions are chemically and physically stable. They can be sterilized by filtration or autoclaving. Sodium chloride will decrease the solubility of some organic compounds; methylparaben is not as soluble in sodium chloride solutions as it is in water.

Methylparaben (Methyl hydroxybenzoate, Methyl parahydroxybenzoate, $C_8H_8O_3$) is available as colorless crystals or as a white crystalline powder that is odorless, or almost odorless, and has a slight burning taste. It is an antimicrobial preservative used in injections (0.065–0.25% concentration), ophthalmic preparations (0.015–0.05% concentration), oral solutions and suspensions (0.015–0.2% concentration), topical preparations (0.02–0.3% concentration) and vaginal preparations (0.1–0.18% concentration). Methylparaben is most effective in solution between pH 4–8 and its efficacy decreases at higher pH levels. The melting point for methylparaben is 125–128 C. and it has a pK of 8.4. One gram is soluble in 400 mL of water, 3 mL of 95% ethanol, 60 mL glycerin, 200 mL peanut oil, 5 mL propylene glycol and it is practically insoluble in mineral oil. In aqueous solution, it can be autoclaved and it is stable in aqueous solution in the pH range of 3–6 for up to four years at room temperature.

Acetic acid contains 36–37% $C_2H_4O_2$. It has a specific gravity of about 1.045 and is miscible with water, alcohol and glycerin. It is used as a solvent and as a buffer component in a sodium acetate:acetic acid buffer system. Sodium acetate, trihydrate occurs as colorless, transparent crystals or as a granular, crystalline powder. It is either odorless or may have a faint, acetous odor. The trihydrate will effloresce in warm, dry air and it melts at about 60° C. It is soluble in water (1 g in 0.8 mL) and alcohol (1 g in 19 mL). It is often used as a component in a sodium acetate:acetic acid buffer.

As an example agent, nonoxynol-9 can be incorporated as a spermicidal agent. Nonoxynol-9 {N-9; α-(4-Nonylphenyl)-ω-hydroxynona(oxyethylene); $C_{33}H_{60}O_{10}$} occurs as a colorless to light yellow, clear viscous liquid with a molecular weight of approximately 616.8. It is soluble in water, alcohol and maize oil. It should be stored in airtight containers. N-9 is used as a vaginal spermicide and it has surface active properties. It also appears to have a protective effective against a number of sexually transmitted diseases. In addition to its spermicidal activity, N-9 also has bacterial activities and has been demonstrated to also provide some protection against the transmission of HIV during sexual intercourse. It is commercially available in products such as Advantage 24 gel (Lake Consumer, 3.5%), Conceptrol gel (Advanced Care, 4%), Delfen foam (Advanced care, 12.5%), Emko foam (Schering-Plough Healthcare, 12%), Encare suppository (Thompson Medical, 100 mg), Gynol jelly (Advanced Care, 2%), Gynol II ES jelly (Advanced Care 3%), Koromex foam (Quality Health, 12.5%), Koromex jelly (Quality Health, 3%), Koromex Crystal Clear gel (Quality Health, 3%), Koromex Inserts suppository (Quality Heal, 125 mg), Ortho-Creme cream (Advanced Care, 2%), Ortho-Gynol jelly (Advanced Care, 1%), Ramses Personal Spermicidal Lubricant gel (London Int'l U.S. Holdings, 3%), Semicid Inserts suppository (Whitehall-Robins Healthcare, 100 mg), Shur-Seal jelly (Milex Products, 2%), VCF gel (Apothecus Pharmaceutical, 3%), VCF Vaginal Contraceptive Film square (Apothecus Pharmaceutical, 28%). Reviews of the use of nonoxynol-9 as a vaginal spermicide have also been published. Compositions of the present invention may comprise agarose present in an amount of from about 0.025 pph to about 10 pph, preferably in an amount of from about 0.05 pph to about 2 pph; carrageenan present in an amount of from about 0.01 pph to about 10 pph, preferably in an amount of about 0.1 pph to about 5 pph; at least one polymer comprising acrylic acid present in an amount of from about 0.02 pph to about 10 pph, preferably in an amount of from about 0.05 pph to about 2.5 pph; methylparaben present in an amount of from about 0.005 pph to about 0.2 pph, preferably present in an amount of from about 0.025 pph to about 0.15 pph; and sodium chloride present in an amount of from about 0.001 pph to about 2 pph, preferably present in an amount of from 0.25 pph to about 1.5 pph.

Therefore, representative, but not limiting, examples of classes of therapeutic agents contemplated by the present invention may be selected from within the group consisting of a spermicide, an antiviral, an antibacterial, an antifungal, an antimycotic, an antipruritic, an emollient, a humectant, an anti-inflammatory, an immunomodulator, a hormonal agent, an antineoplastic and an analgesic.

The following examples are provided to illustrate the present invention and are not to be construed as limiting the invention in any manner.

EXAMPLES

The examples disclosed provide formulations of illustrative compositions for the bioadhesive prolonged release drug composition comprising different therapeutic agents. Individual components of the formulations are combined as described in the Examples below. Generally, the product is prepared by first dissolving the rapidly soluble ingredients, such as sodium chloride, buffers and the preservative; this is done prior to the addition of the agents which will increase the viscosity of the system. The gelling agents are then added, followed by the polycarbophil or other polyacrylic acid polymer. Heat is used to increase the hydration rate of the ingredients followed by cooling and adjustment of the mixture to the final volume. The therapeutic agent is added either in the first step or in the last step of the process, depending upon whether heating will be required for effective dissolution or dispersion of the specific therapeutic agent included or upon the thermal sensitivity of that material. All reagent levels are reported as parts per hundred (pph), that is, as grams of reagent per 100 mL of solution. In all of the examples presented below, purified water is added in a quantity sufficient to bring the mixture to a final volume of 100 mL. Furthermore, each of the mixtures comprises 20 mM acetate buffer, pH 4.5.

Example 1

To prepare 100 g of material: Accurately weigh each of the ingredients. Add the sodium chloride, methylparaben, and acetate buffer [to provide a final concentration of 20 mM acetate buffer, pH 4.5] to about 40 mL of purified water using a stirring system at room temperature. Add the Ultra Low Gelling Temperature Agarose slowly, with continued stirring at room temperature, until dispersed; add the Carrageenan slowly until dispersed and allow to continue to stir for about one hour. Add the Polycarbophil until dispersed and heat to about 90° C. for about five minutes, and then cool to 70° C. with continued stirring for another five minutes. Adjust the final volume to 100 mL after further cooling to room temperature. Stir until a uniform mixture is obtained.

| Reagent | Grams per 100 mL. Solution |
| --- | --- |
| Carrageenan | 1.0 |
| Ultra Low Gelling Temperature Agarose | 0.25 |
| Polycarbophil/Polyacrylic Acid Polymers | 0.20 |
| Methylparaben | 0.10 |
| Sodium chloride | 0.90 |

Example 2

The procedures are as in Example 1, except that the following ingredients are combined in the stated amounts.

| Reagent | Grams per 100 mL. Solution |
| --- | --- |
| Carrageenan | 1.5 |
| Ultra Low Gelling Temperature Agarose | 0.20 |
| Polycarbophil | 0.20 |
| Methylparaben | 0.10 |
| Sodium chloride | 0.90 |

Example 3

The procedures are as in Example 1, except that the following ingredients are combined in the stated amounts.

| Reagent | Grams per 100 mL. Solution |
| --- | --- |
| Carrageenan | 2.0 |
| Ultra Low Gelling Temperature Agarose | 0.15 |
| Polycarbophil | 0.20 |
| Methylparaben | 0.10 |
| Sodium chloride | 0.90 |

Example 4

To prepare 100 g of material: Add the sodium chloride, methylparaben, acetate buffer [to provide a final concentration of 20 mM acetate buffer, pH 4.5] to about 40 mL of purified water using a stirring system at room temperature. Add the Ultra Low Gelling Temperature Agarose slowly, with continued stirring, at room temperature until dispersed; add the Carrageenan slowly until dispersed and allow to continue to stir at room temperature for about one hour. Add the Polycarbophil until dispersed and heat to about 90° C. for about five minutes, then cool to 70° C., with continued stirring, for another five minutes. Add the nonoxynol-9 and mix well. Adjust the final volume to 100 mL after further cooling to room temperature. Stir until a uniform mixture is obtained.

| Reagent | Grams per 100 mL. Solution |
|---|---|
| Nonoxynol-9 | 6.67 |
| Carrageenan | 1.0 |
| Ultra Low Gelling Temperature Agarose | 0.25 |
| Polycarbophil | 0.20 |
| Methylparaben | 0.10 |
| Sodium chloride | 0.90 |

Example 5

To prepare 100 g of material: Add the sodium chloride, methylparaben, and acetate buffer [to provide a final concentration of 20 mM acetate buffer, pH 4.5] to about 40 mL of purified water using a stirring system at room temperature. Add the Ultra Low Gelling Temperature Agarose slowly, with continued stirring at room temperature, until dispersed; add the Carrageenan slowly until dispersed and allow to continue to stir at room temperature, for about one hour. Add the Polyacrylic acid polymer until dispersed and heat to about 90° C. for about five minutes, then cool to 70° C. with continued stirring for another five minutes. Add the nonoxynol-9 and mix well. Adjust the final volume to 100 mL after further cooling to room temperature. Stir until a uniform mixture is obtained.

| Reagent | Grams per 100 mL. Solution |
|---|---|
| Nonoxynol-9 | 6.67 |
| Carrageenan | 1.0 |
| Ultra Low Gelling Temperature Agarose | 0.25 |
| Polyacrylic Acid Polymer (Pemulen) | 0.20 |
| Methylparaben | 0.10 |
| Sodium chloride | 0.90 |

Example 6

The procedures are as in Example 1, except that the following ingredients are combined in the stated amounts.

| Reagent | Grams per 100 mL. Solution |
|---|---|
| Carrageenan | 2.0 |
| Ultra Low Gelling Temperature Agarose | 0.15 |
| Polyacrylic Acid Polymers | 0.20 |
| Methylparaben | 0.10 |
| Sodium chloride | 0.90 |

Example 7

The procedures are as in Example 1, except that the following ingredients are combined in the stated amounts.

| Reagent | Grams per 100 mL. Solution |
|---|---|
| Carrageenan | 1.5 |
| Ultra Low Gelling Temperature Agarose | 0.20 |
| Polyacrylic Acid Polymers | 0.20 |
| Methylparaben | 0.10 |
| Sodium chloride | 0.90 |

Example 8

The procedures are as in Example 1, except that the following ingredients are combined in the stated amounts.

| Reagent | Grams per 100 mL. Solution |
|---|---|
| Nonoxynol-9 | 6.67 |
| Carrageenan | 1.5 |
| Ultra Low Gelling Temperature Agarose | 0.20 |
| Polycarbophil | 0.20 |
| Methylparaben | 0.10 |
| Sodium chloride | 0.90 |

Example 9

The procedures are as in Example 1, except that the following ingredients are combined in the stated amounts.

| Reagent | Grams per 100 mL. Solution |
|---|---|
| Nonoxynol-9 | 6.67 |
| Carrageenan | 1.5 |
| Ultra Low Gelling Temperature Agarose | 0.20 |
| Polyacrylic Acid Polymer (Pemulen) | 0.20 |
| Methylparaben | 0.10 |
| Sodium chloride | 0.90 |

Example 10

The procedures are as in Example 1, except that the following ingredients are combined in the stated amounts.

| Reagent | Grams per 100 mL. Solution |
|---|---|
| Nonoxynol-9 | 6.67 |
| Carrageenan | 2.0 |
| Ultra Low Gelling Temperature Agarose | 0.20 |
| Polyacrylic Acid Polymer (Pemulen) | 0.20 |
| Methylparaben | 0.10 |
| Sodium chloride | 0.90 |

Example 11

The procedures are as in Example 1, except that the following ingredients are combined in the stated amounts.

| Reagent | Grams per 100 mL. Solution |
|---|---|
| Nonoxynol-9 | 6.67 |
| Carrageenan | 2.25 |

-continued

| Reagent | Grams per 100 mL. Solution |
|---|---|
| Ultra Low Gelling Temperature Agarose | 0.35 |
| Polycarbophil | 0.25 |
| Methylparaben | 0.10 |
| Sodium chloride | 0.90 |

Example 12

The procedures are as in Example 1, except that the following ingredients are combined in the stated amounts.

| Reagent | Grams per 100 mL. Solution |
|---|---|
| Nonoxynol-9 | 6.67 |
| Carrageenan | 2.25 |
| Ultra Low Gelling Temperature Agarose | 0.35 |
| Polyacrylic Acid Polymer (Pemulen) | 0.25 |
| Methylparaben | 0.10 |
| Sodium chloride | 0.90 |

What is claimed is:

1. A prolonged-release bioadhesive drug composition comprising:
    carrageenan;
    at least one polymer comprising acrylic acid;
    agarose; and
    a therapeutically effective amount of at least one therapeutic agent.

2. The composition of claim 1, wherein the therapeutic agent is released at an initial non-linear rapid rate of release followed by a second slower, linear rate of release characterized by a biphasic zero order release profile.

3. The composition of claim 1, wherein the therapeutic agent is released for up to about 24 hours.

4. The composition of claim 1, wherein the agarose is ultra low gelling temperature agarose.

5. The composition of claim 4, wherein the agarose is present in an amount of from about 0.025 pph to about 10 pph.

6. The composition of claim 4, wherein the agarose is present in an amount of from about 0.05 pph to about 2 pph.

7. The composition of claim 1, wherein the carrageenan is present in an amount of from about 0.01 pph to about 10 pph.

8. The composition of claim 7, wherein the carrageenan is present in an amount of from about 0.1 pph to about 5 pph.

9. The composition of claim 1, wherein the at least one polymer comprising acrylic acid is selected from the group consisting of copolymers of acrylic acid, polycarbophil, homopolymers of acrylic acid crosslinked with divinyl glycol, polyacrylic acid homopolymers, carbomers, Carbopol 974P-NF, Carbopol 971P-NF, easy-to-disperse resins and copolymers of acrylic acid and $C_{10}$ to $C_{30}$ alkyl acrylic acid.

10. The composition of claim 9, wherein the at least one polymer comprising acrylic acid is present in an amount of from about 0.02 pph to about 10 pph.

11. The composition of claim 1, wherein the at least one polymer comprising acrylic acid is present in an amount of from about 0.05 pph to about 2.5 pph.

12. The composition of claim 1, further comprising methylparaben, wherein the methylparaben is present in an amount of from about 0.005 pph to about 0.2 pph.

13. The composition of claim 12 wherein the methylparaben is present in an amount of from about 0.025 pph to about 0.15 pph.

14. The composition of claim 1, further comprising sodium chloride, wherein the sodium chloride is present in an amount of from about 0.001 pph to about 2 pph.

15. The composition of claim 14, wherein the sodium chloride is present in an amount of from about 0.25 pph to about 1.5 pph.

16. The composition of claim 1, wherein the therapeutic agent is selected from the group consisting of a spermicide, an antiviral, an antibacterial, an antifungal, an antimycotic, an antipruritic, an emollient, a humectant, an antiinflammatory, an immunomodulator, a hormonal, an antineoplastic and an analgesic.

17. The composition of claim 1, wherein the therapeutic agent is nonoxynol-9.

18. A method of administering a therapeutic agent comprising:
    providing a bioadhesive, prolonged release drug composition comprising
    carrageenan;
    at least one polymer comprising acrylic acid;
    agarose;
    an effective amount of at least one therapeutic agent; and
    contacting mammalian vaginal mucosa with the composition.

19. The method of claim 18, wherein the at least one therapeutic agent is released at an initial non-linear rapid rate of release followed by a second slower, linear rate of release, characterized by a biphasic zero order release profile.

20. The method of claim 18, wherein the agarose is ultra low gelling temperature agarose.

21. The method of claim 18, wherein the at least one polymer comprising acrylic acid is selected from the group consisting of copolymers of acrylic acid, polycarbophil, homopolymers of acrylic acid crosslinked with divinyl glycol, polyacrylic acid homopolymers, carbomers, Carbopol 974P-NF, Carbopol 971P-NF, easy-to-disperse resins and copolymers of acrylic acid and $C_{10}$ to $C_{30}$ alkyl acrylic acid.

22. The method of claim 18, wherein the therapeutic agent is selected from the group consisting of a spermicide, an antiviral, an antibacterial, an antifungal, an antimycotic, an antipruritic, an emollient, a humectant, an antiinflammatory, an immunomodulator, a hormonal, an antineoplastic and an analgesic.

23. A method for making a bioadhesive, prolonged release drug composition comprising the steps of:
    (a) dissolving appropriate amounts of soluble components comprising sodium chloride, methylparaben, acetate buffer, and, optionally, at least one therapeutic agent, in water to provide a first mixture;
    (b) dispersing appropriate amounts of gelling agents comprising agarose and carrageenan in the first mixture to provide a second mixture, wherein the second mixture is stirred about one hour;
    (c) dispersing an appropriate amount of at least one polymer comprising acrylic acid in the second mixture providing a third mixture, wherein the third mixture is stirred and heated to at least about 90° C., and wherein the third mixture is further cooled and stirred at about 70° C.; and
    (d) cooling the third mixture to room temperature and stirring the third mixture until uniform, and, optionally, adding at least one therapeutic agent.

24. The method of claim 23, wherein the agarose is ultra low gelling temperature agarose.

25. The method of claim 23, wherein at least one polymer comprising acrylic acid is selected from the group consisting of copolymers of acrylic acid, polycarbophil, homopolymers of acrylic acid crosslinked with divinyl glycol, polyacrylic acid homopolymers, carbomers, Carbopol 974P-NF, Carbopol 971P-NF, easy-to-disperse resins and copolymers of acrylic acid and $C_{10}$ to $C_{30}$ alkyl acrylic acid.

26. The method of claim 23, wherein the therapeutic agent is selected from the group consisting of a spermicide, an antiviral, an antibacterial, an antifungal, an antimycotic, an antipruritic, an emollient, a humectant, an anti-inflammatory, an immunomodulator, a hormonal, an antineoplastic and an analgesic.

27. The method of claim 23, wherein the therapeutic agent is nonoxynol-9.

* * * * *